(12) United States Patent
Doerr et al.

(10) Patent No.: US 9,079,038 B2
(45) Date of Patent: Jul. 14, 2015

(54) IMPLANTABLE DEVICE WITH ELONGATED ELECTRICAL CONDUCTOR

(75) Inventors: Thomas Doerr, Berlin (DE); Ingo Weiss, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 905 days.

(21) Appl. No.: 13/301,686

(22) Filed: Nov. 21, 2011

(65) Prior Publication Data

US 2012/0157813 A1 Jun. 21, 2012

Related U.S. Application Data (60) Provisional application No. 61/424,685, filed on Dec. 20, 2010.

(51) Int. Cl.
| | |
|---|---|
| *A61N 1/05* | (2006.01) |
| *A61N 1/37* | (2006.01) |
| *A61N 1/08* | (2006.01) |
| *A61B 18/14* | (2006.01) |

(52) U.S. Cl.
CPC .......... *A61N 1/3718* (2013.01); *A61B 18/1492* (2013.01); *A61N 1/056* (2013.01); *A61N 1/08* (2013.01); *A61N 2001/086* (2013.01)

(58) Field of Classification Search
CPC ... A61N 1/056; A61N 1/08; A61N 2001/086; A61B 18/1492
USPC ............................ 600/374; 607/119, 122, 123
See application file for complete search history.

(56) References Cited

U.S. PATENT DOCUMENTS

| | | | |
|---|---|---|---|
| 4,387,717 A | 6/1983 | Brownlee et al. | |
| 4,532,934 A | 8/1985 | Kelen | |
| 5,218,961 A * | 6/1993 | Lekholm | 607/22 |
| 2003/0204207 A1 | 10/2003 | MacDonald et al. | |

FOREIGN PATENT DOCUMENTS

GB 1410743 10/1975

OTHER PUBLICATIONS

European Search Report dated Mar. 27, 2013, 5 pages.

* cited by examiner

*Primary Examiner* — Tammie K Heller
(74) *Attorney, Agent, or Firm* — ARC IP Law, PC; Joseph J. Mayo (57) ABSTRACT

An implantable medical device having at least one elongated electrical function conductor and an electrode pole connected to the at least one elongated function conductor. The at least one elongated function conductor transmits therapeutic signals or diagnostic signals or both. The electrode pole delivers electrical current or field or sense electrical potentials, or both, in surrounding tissue during use. The implantable medical device includes a sensing device connected to a field-generating electrode pole, a potential-sensing electrode pole, and a reference pole. The sensing device detects generated electrical potentials via the potential-sensing electrode pole in relation to the reference pole, and generates an output signal that represents a detected electrical potential. The implantable medical device includes a control device connected to the sensing device to evaluate an output signal generated by the sensing device, and to control the medical device as a function of the potential detected by the sensing device.

15 Claims, 6 Drawing Sheets

IMPLANTABLE DEVICE WITH ELONGATED ELECTRICAL CONDUCTOR

This application claims the benefit of U.S. Provisional Patent Application 61/424,685 filed on 20 Dec. 2010, the specification of which is hereby incorporated herein by reference.

BACKGROUND OF THE INVENTION

1. Field of the Invention

At least one embodiment of the invention relates to a permanently or temporarily implantable device having an elongated electrical conductor.

2. Description of the Related Art

Such devices, for example electrode lines for electrostimulation, have the disadvantage that their electrical conductor may heat up during magnetic resonance imaging due to the fact that the alternating magnetic fields that are present induce considerable electrical currents in the electrical conductor. In addition, such induced currents may be delivered to surrounding tissue via electrode poles of the electrode line, resulting in undesired heating of the tissue, for example. For this reason, there is presently little or no possibility for cardiac pacemaker patients to be tested using magnetic resonance imaging.

Implantable cardiac pacemakers or defibrillators (also jointly referred to below as cardiac stimulators or implantable pulse generators (IPG)) are typically connected to at least one stimulation electrode line, which at its proximal end which is provided for connection to the cardiac pacemaker or defibrillator has a standardized electrical terminal, and at its distal end which is provided for placement in the heart has one or more electrode poles. Such an electrode pole is used to deliver electrical pulses to the (myocardial) tissue of the heart or for sensing electrical fields in order to sense an activity of a heart. For these purposes, electrode poles typically form electrically conductive surface sections of an electrode line. Electrode poles are typically provided as an annular electrode in the form of a ring around the electrode line, or in the form of a point electrode or tip electrode at the distal end of the electrode line. At their proximal end the electrode poles are connected in an electrically conductive manner via one or more electrical conductors to contacts of the electrical terminal of the electrode line. Thus, the electrode lines at their proximal end extend between the contacts of the electrical terminal, and at the distal end one or more electrical conductors which electrically connect the one or more electrode poles to the one or more contacts extend between the electrode poles. These electrical conductors may be used on the one hand for transmitting stimulation pulses to the electrode poles, and on the other hand for transmitting electrical signals received via the electrode poles to the proximal end of the electrode line, and in the description below are also referred to in each case as a function line. Such function lines are electrical conductors which are necessary for the functions of the particular electrode line, and are thus subject to the risk of electrical currents being induced therein as the result of external alternating magnetic fields which, for example, may lead to undesired heating of the function lines or the electrode poles connected thereto, or may result in the discharge of corresponding currents via the electrode poles to surrounding tissue, and thus heating of the surrounding tissue.

BRIEF SUMMARY OF THE INVENTION

The object of at least one embodiment of the invention is to provide a device which eliminates the above-described problem.

According to at least one embodiment of the invention, this object is achieved by a permanently or temporarily implantable medical device having at least one elongated electrical function conductor for transmitting therapeutic signals or diagnostic signals or both, and an electrode pole connected to the function conductor by means of which electrical current may be delivered to surrounding bodily tissue during use, or by means of which electrical potentials may be sensed in surrounding tissue during use, or both, wherein a sensing device is provided which is connected to a field-generating electrode pole and to a potential-sensing electrode pole, and which in the event of a current output via the field-generating electrode pole is designed to detect generated electrical potentials via the potential-sensing electrode pole in relation to a reference potential, and to generate an output signal which represents a detected electrical potential, and a control device which is connected to the sensing device and is designed to evaluate an output signal generated by the sensing device, and to control the medical device as a function of the potential detected by the sensing device.

At least one embodiment of the invention includes an implanted system having a connected electrode line having at least two electrode poles, or an elongated electronic implant having electrode poles whose electrical field of the one electrode pole, as a field-generating electrode pole which is able to heat the surrounding tissue as the result of induced currents, for example by interaction in magnetic resonance imaging (MRI), is sensed by a further electrode pole system as sensing electrode poles, and generates one or more signals which is/are evaluated by a device connected to the electrode poles, and which is/are used for activating the implant with regard to a safety measure.

Since the potential which is to be detected is a potential resulting from high-frequency, external interference fields, the potential itself is a signal having a high-frequency signal curve.

The field-generating electrode pole may at the same time be one of the sensing electrode poles, which includes at least one reference pole as a further electrode pole which supplies the reference potential.

Electrode poles which are mounted anyway on the electrode as therapeutic/diagnostic poles are preferably selected as nonfield-generating, sensing electrode poles, so that no additional electrode poles are necessary.

The implant-side input which is provided for connection to the field-generating electrode pole is preferably used as the reference potential-supplying reference pole for the signal of the sensing electrode pole.

Alternatively, an implant-side input which is provided for connection to a third electrode pole may be used as the reference potential-supplying reference pole for the signal of the sensing electrode pole.

Alternatively, an electrode pole formed by an implant housing may be provided as the reference potential-supplying reference pole for the signal of the sensing electrode pole.

In principle, the medical device may also be designed to process a combination of various signals which originate, for example, from various sensing electrode poles with respect to different reference potentials. For this purpose, the sensing device may include a mixer for combining signals. Alternatively, an evaluation unit or evaluation device of the sensing unit may be designed to process the various signals in parallel, i.e., unmixed. A higher degree of interference immunity results in both cases.

The evaluation device may also be designed to evaluate only signals in specific frequency ranges, for example signals >1 MHz, or bands with bandwidths of <5 MHz around typical MRI HF frequencies such as 42, 64, 128 MHz, for example. The sensing device may have an appropriate filter for this purpose.

Furthermore, the evaluation device may be designed to evaluate only signals above a specific threshold, for example in the frequency range around 64 MHz >1V.

An electrode pole having low heating potential, i.e., an electrode pole for which a low degree of interference is expected, is preferably provided as the sensing electrode pole. The evaluation device may be designed to select the sensing electrode pole among the available electrode poles. For example, a tip electrode of a coaxially configured standard electrode may be selected as a field-generating electrode pole. An annular electrode is correspondingly selected as a sensing electrode pole.

According to one preferred embodiment variant, the selection of the electrode poles (field-generating, sensing) is externally programmable.

The evaluation device may be designed to determine the cumulative effect of the signal which represents the detected potential, for example by integration, averaging, or determining the effective value.

Alternatively, the evaluation device may be designed to determine the maximum effect of the signal, generally pulsed, which represents the detected potential, and for this purpose may be designed as a maximum value detector, for example.

The control device is preferably designed to switch the medical device and/or the implant-side electrode circuitry to a safe mode for the particular operating environment, in particular in the event of an extreme electromagnetic field effect, in response to a corresponding output signal of the evaluation device when the output signal of the evaluation device indicates such an operating environment. The control device is preferably designed to perform this switching in a time-limited manner, for example for a specific, programmable period of time, or for a latency period following the last recorded interference.

According to another preferred embodiment variant, the medical device may have a telemetry device which is at least indirectly connected to the evaluation device. In this case the evaluation device is preferably designed to externally communicate the occurrence of electrode heating above a threshold, or an electrical signal amplitude indicating such, via the telemetry device. This may be carried out in real time, or after analysis for providing information to the medical practitioner via a home monitoring system, for example.

The medical device, in particular when it has the form of an electrode line, preferably has a converter which is distally located in the immediate proximity of the sensing electrode poles, and which converts the signal energy detected at the sensing electrode poles for more efficient (undisturbed) transmission to the evaluation unit.

The converter may be a transformer which transforms the signal representing the detected potentials to a higher value in order to conduct the signal via high-impedance lines, and therefore with immunity to RF interference, to the evaluation unit.

Alternatively, the converter may be a piezoelectric converter or in general an electroacoustic converter which converts detected potentials to mechanical signals, so that they may be conducted acoustically, i.e., mechanically and therefore with immunity to RF interference, to the evaluation unit.

According to another alternative, the converter is a rectifier or demodulator which converts the detected potentials to a useful signal in the form of a direct current signal. Any interferences (RF) may then be easily filtered out upstream from the evaluation unit.

Another alternative provides a converter in the form of an electrooptical converter, for example a light-emitting diode (LED), which converts detected potentials to a useful signal in the form of a light signal which may then be conducted without interference to the evaluation device. When the useful signal is a mechanical, in particular acoustic, or an optical useful signal, a second converter may be provided in the vicinity of the evaluation unit, for example at the proximal end of an electrode line, which converts the particular useful signal back to an electrical signal. The sensitivity to interference is correspondingly reduced due to the fact that this advantageously occurs just upstream from the evaluation unit.

In addition to the embodiments described herein other alternative embodiments may include some or all of the disclosed features.

BRIEF DESCRIPTION OF THE DRAWINGS

At least one embodiment of the invention is explained in greater detail with reference to the figures, which show the following.

DETAILED DESCRIPTION OF THE INVENTION

Figure 1:
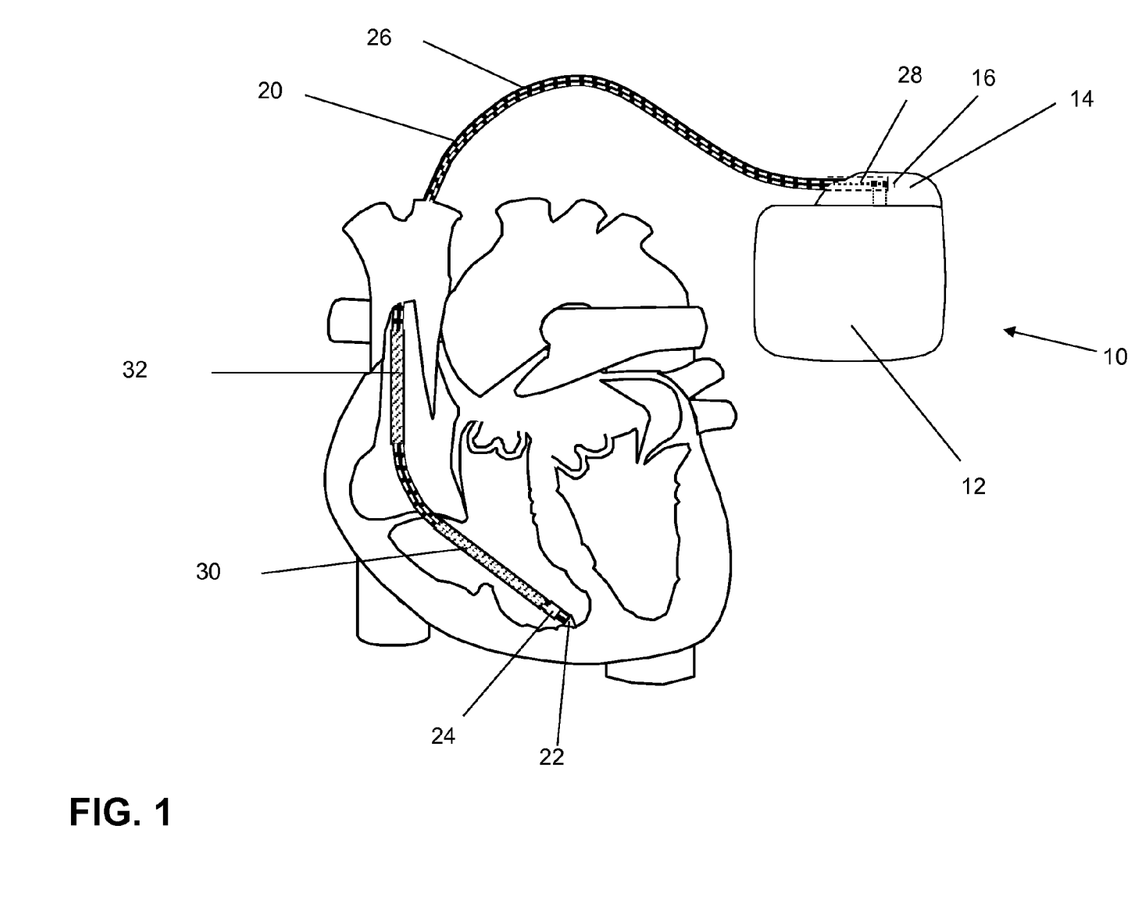
FIG. 1 shows as an implantable medical device an implantable cardiac stimulator 10 and an implantable electrode line 20 connected thereto.

The implantable cardiac stimulator 10 may be a cardiac pacemaker or a cardioverter/defibrillator (ICD). In the illustrated exemplary embodiment, the cardiac stimulator 10 is a ventricular cardiac pacemaker and defibrillator. Other known cardiac stimulators are dual-chamber cardiac pacemakers for stimulating the right atrium and the right ventricle, or biventricular cardiac pacemakers, which in addition to the right ventricle are also able to stimulate the left ventricle.

Such stimulators typically have a housing 12, which is generally made of metal and is therefore electrically conductive, and which may be used as a large-surface electrode pole. A connector housing 14, also referred to as a header, is typically affixed to the exterior of the housing 12. Such a header typically has contact sockets for accommodating plug contacts. The contact sockets have electrical contacts 16 which are connected via appropriate conductors to an electronics system situated in the housing 12 of the cardiac stimulator 10.

The electrode line 20 likewise represents an implantable medical device within the meaning of at least one embodiment of the invention. Electrode poles in the form of a point electrode or tip electrode 22 and an annular electrode 24 present in the vicinity thereof are situated in a manner known per se at the distal end of the electrode line 20. The electrode poles 22 and 24 are designed in such a way that, depending on the function of a cardiac stimulator to which the electrode line 20 is connected, they are provided to sense electrical potentials of the cardiac tissue (myocardium) or to supply electrical signals, for example for delivering stimulation pulses to the cardiac tissue which surrounds them. FIG. 1 shows the manner in which the electrode poles, i.e., the tip electrode 22 and the annular electrode 24, and for the present application, the electrode line 20, are located in the apex of a right ventricle of a heart.

The tip electrode 22 and the annular electrode 24 are in each case electrically connected via at least one electrical conductor 26 to a plug contact 28 at the proximal end of the electrode line 20. The plug contact 28 has electrical contacts which correspond to the electrical contacts 16 of the contact socket in the connector housing 14 of the implantable cardiac stimulator. The electrical conductors 26 in the electrode line 20 may be designed as somewhat elongated cable conductors or as helically coiled conductors. Such conductors, which connect functional electrode poles to electrical contacts of the plug contact at the proximal end of the electrode line 20 in an electrically conductive manner, are referred to as function conductors within the scope of this description, since, for example, they transmit electrical signals used for the treatment from the plug contact to the particular electrode pole, or conduct sensed signals which represent electrical potentials from the particular electrode pole to the plug contact, and are thus used for the fundamental function of the medical device.

The electrical conductors 26 which connect the electrode poles 22 and 24 to the electrical contacts of the plug 28 of the electrode line 20 are enclosed over most of their length by an insulating sheath, resulting in targeted electrical contact with the tissue of the heart via the electrode poles.

In addition to the electrode poles 22 and 24, which are typically used for stimulation (in this case, ventricular) of the cardiac tissue, the electrode line 20 has two large-surface electrode poles 30 and 32, which are used as defibrillation electrodes and are formed by at least one bare helically wound wire.

It is pointed out that within the scope of this exemplary embodiment the invention is explained with reference to a right ventricular cardiac pacemaker and defibrillator. As a medical device within the meaning of at least one embodiment of the invention, however, in principle an ablation electrode line may also be used, which in the application likewise extends into the heart of a patient and is controlled by a device located outside the patient, and for this purpose is connected to the device.

Figure 2:
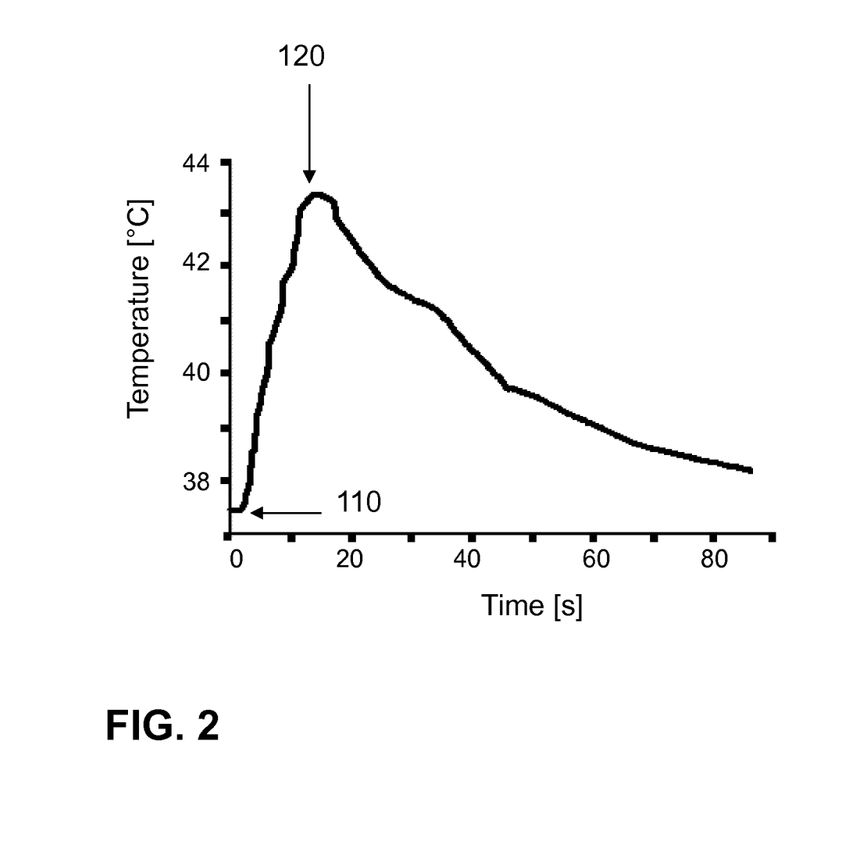
FIG. 2 shows a typical temperature curve at the electrode tip.

FIG. 2 illustrates a typical temperature curve 100 of a conventional pacemaker/ICD electrode in magnetic resonance imaging (MRI). The temperature increases rapidly when the high-frequency alternating field in the MRI unit is switched on at time 110, the steepness of the increase and the maximum achievable temperature being greatly dependent on the electrode position relative to the high-frequency alternating fields of the MRI. When the high-frequency alternating field is switched off at time 120, the electrode tip quickly cools due to its relatively low heat capacity.

Figure 3:
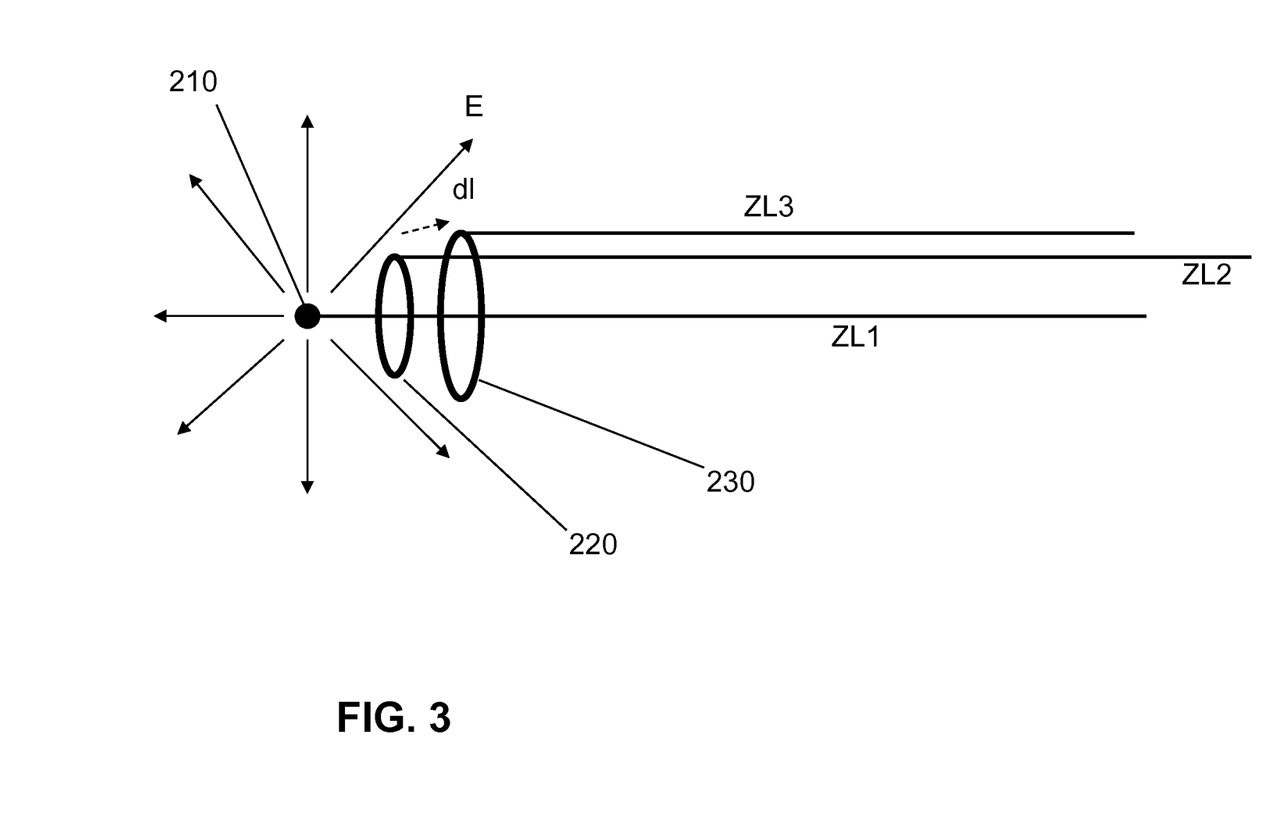
FIG. 3 shows an example of how a field-generating electrode pole (tip electrode) of a conductor having intense interference injection cooperates with sensing electrode poles in the form of annular electrodes. E*dl results in a voltage which is a measure of the field strength E, and thus of the heating of the tip.

FIG. 3 schematically shows an electrode pole in the form of a tip electrode 210, and two electrode poles in the form of annular electrodes 220 and 230, each of which is connected to a function conductor (supply line) ZL1, ZL2, and ZL3, respectively. The schematically illustrated electrode poles are typically located at the distal end of an electrode line, which also has further components, for example an insulating sheath, which are not shown in the schematic illustration. It is known that the function conductors ZL1, ZL2 or ZL3 may assume various shapes, and may be designed as cable feeds or also as helically shaped feeds. FIG. 3 shows the manner in which a field-generating electrode pole, in this case the tip electrode 210, cooperates with sensing electrode poles in the form of annular electrodes 220 and 230 when the function conductors ZL1, ZL2, ZL3 are exposed to intense interference injection, for example as the result of externally acting high-frequency alternating fields in a magnetic resonance imaging (MRI) unit. The electrical field around the tip electrode 210 is indicated by arrows and the letter E. The product of E and the distance dl (E*dl) results in the voltage which is present between the annular electrodes 220 and 230 due to the field, having field strength E, emanating from the tip electrode 210. Thus, a measure of the field strength of the electrical field E around the tip electrode 210 may be derived from the difference in potentials between the annular electrodes 220 and 230.

Figure 4A:
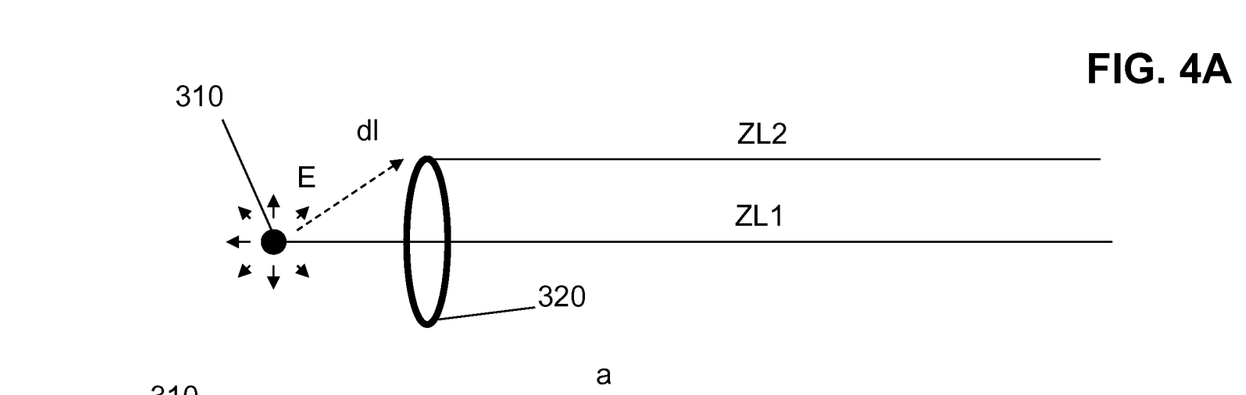
FIGS. 4A and 4B show fields at the electrode tip; the field-generating electrode pole (in this case, the tip electrode) is at the same time one of the sensing poles in this instance.
Figure 4B:
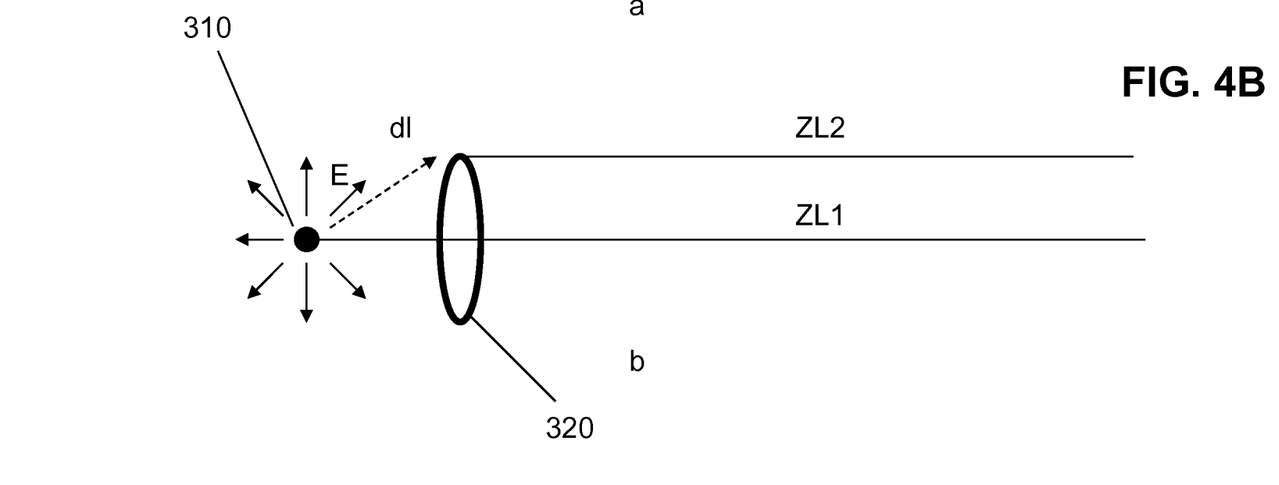

The tip electrodes and annular electrodes 310 and 320, respectively, and their respective supply lines (function conductors) ZL1 and ZL2 are schematically illustrated in FIGS. 4A and 4B, similarly as in FIG. 3.

FIGS. 4A and 4B show that the current intensity emanating at the electrode pole is of different magnitudes, depending on the strength of the acting electromagnetic fields. This is correlated with a change in the strength of the electrical field E as well as the heating which is produced. For coaxial electrode lines (the predominant design in current clinical practice), for example the degree of heating (and therefore the electrical field) of the annular electrode(s) is usually much lower than that of the tip electrode. Therefore, it may be ignored as an approximation. However, the annular electrode(s) 320 is/are located in the field of the tip electrode 310, and are therefore at a different potential as a function of the field strength. The corresponding voltage is calculated from the integral $\int E(l) dl$. This signal reaches the IPG via function line ZL2 (the supply line for the annular electrode 320), where it may be evaluated. The fact that the annular electrode(s) is/are at a given potential in the field of the tip electrode may be determined in relation to other reference potentials (thus, for example, the tip itself, another ring, or the IPG housing).

Figure 5A:
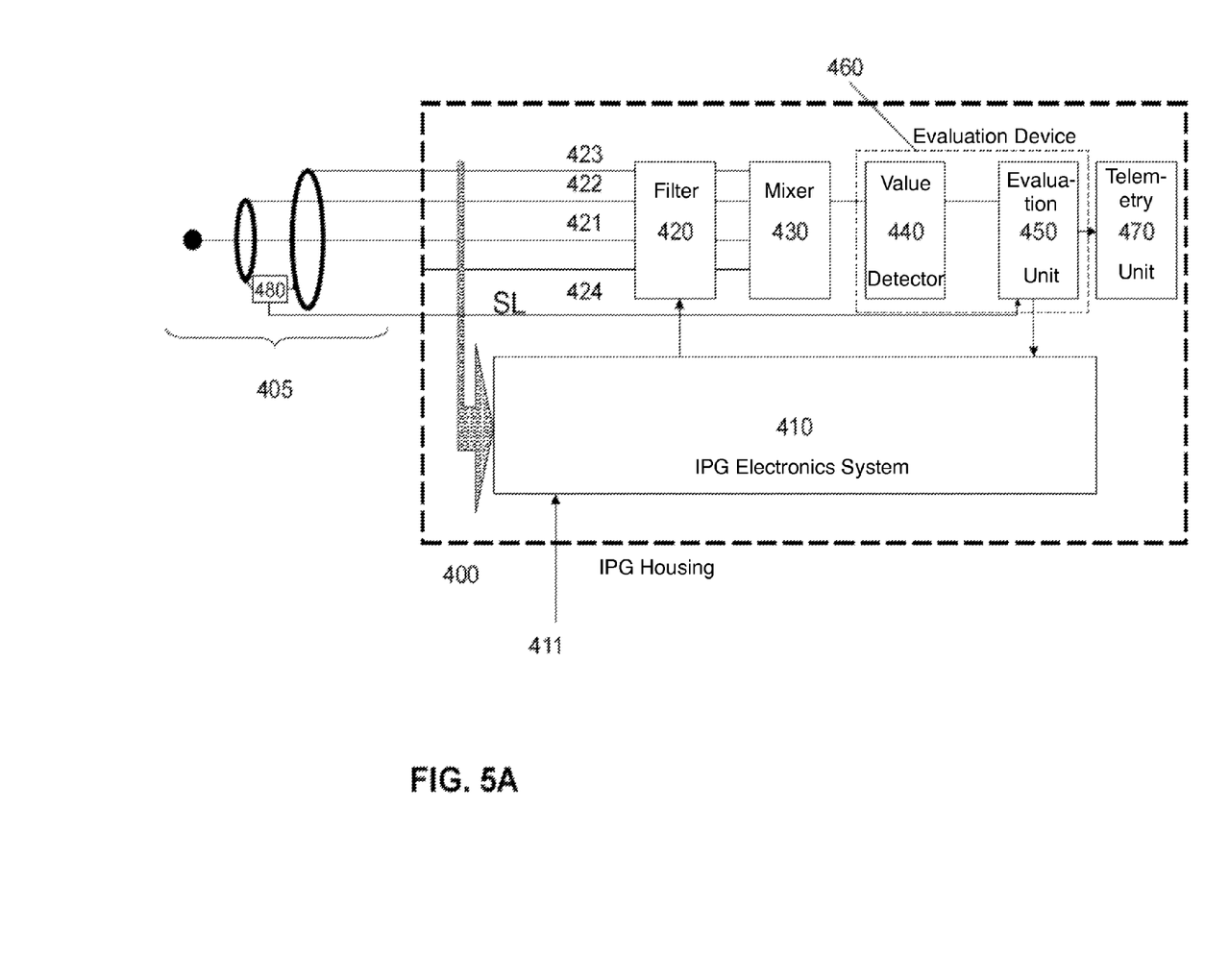
FIGS. 5A and 5B show two variants of an implantable pulse generator, each having a device for evaluating an electrical signal of the electrode, which is correlated with the heating of an electrode pole.
Figure 5B:
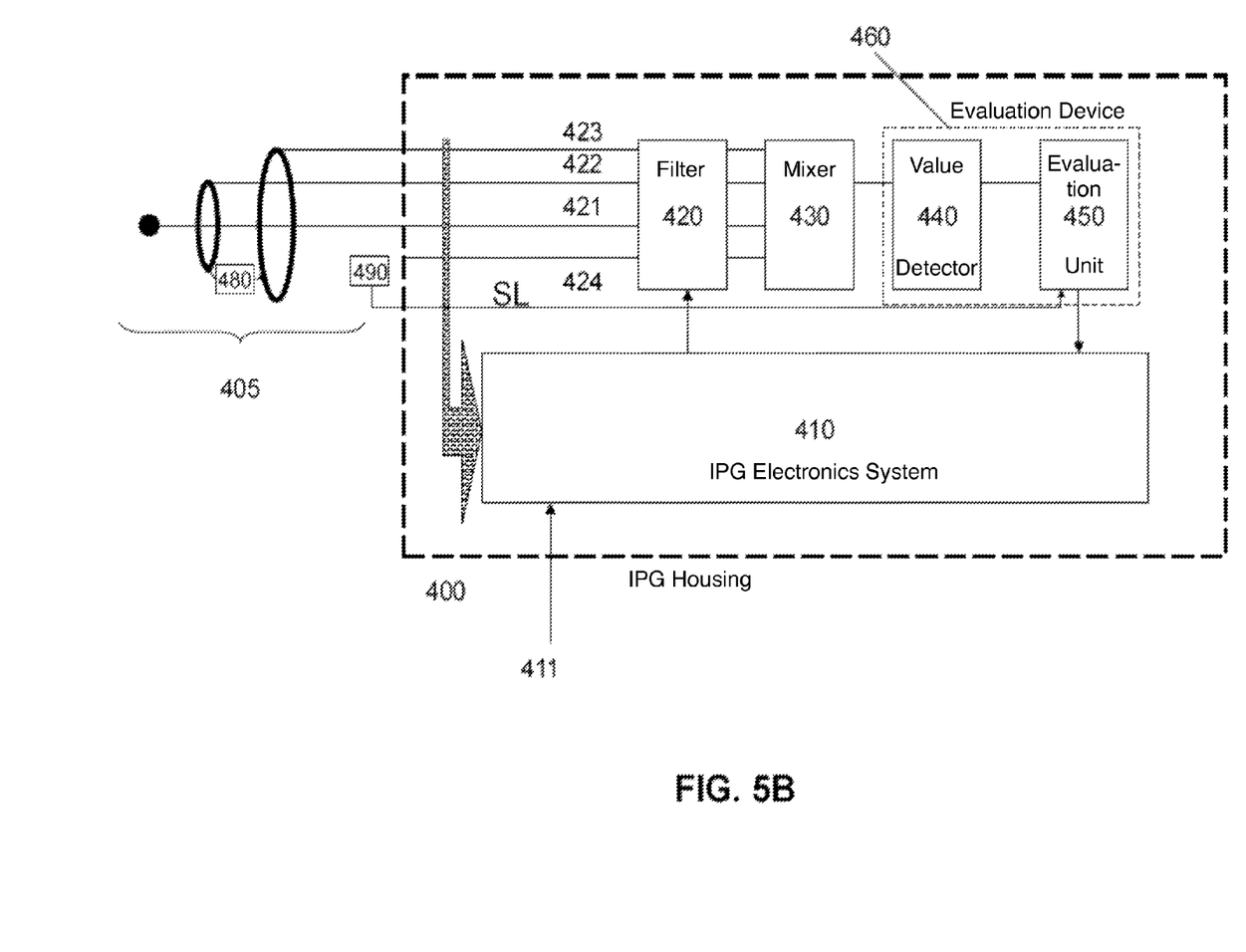

FIGS. 5A and 5B each show a block diagram of the cardiac stimulator 10, which in the present case is referred to as an implantable pulse generator (IPG). The IPG has a sensing device for evaluating an electrical signal of the electrode which is correlated with the heating of an electrode pole.

The IPG housing 400 of the cardiac stimulator 10 is schematically indicated in FIGS. 5A and 5B. The components which are relevant to the present exemplary embodiment are illustrated as blocks in the IPG housing 400. Therefore, the possibility of further components of a typical cardiac stimulator being present in addition to the illustrated components is not excluded. An electrode line 405 is connected to the IPG housing 400. The electrode line 405 is likewise schematically illustrated in the sense of the diagram in FIG. 3, and in the illustrated exemplary embodiment has an electrode pole in the form of a tip electrode, and two electrode poles in the form of annular electrodes, each of which is connected via its own supply line (function conductor) 421, 422, 423, respectively, to an optional filter 420. A mixer 430 is connected downstream from the optional filter 420, and downstream from the mixer 430 is a threshold value detector 440. The output signal of the threshold value detector 440 is delivered to an evaluation unit 450, which in turn acts on the remaining electronics system of the cardiac pacemaker, referred to in general as the IPG electronics system 410. The arrow 411 indicates that the IPG electronics system 410 is externally programmable.

The function conductor (supply lines) 421-423 of the electrode line 405 extend to the interior of the IPG, and arrive at that location. The optional filter 420 results in only signals in specific frequency ranges, for example greater than 1 MHz, or bands having bandwidths of less than 10 MHz around typical magnet resonance HF frequencies such as 42, 64, 128 MHz, for example, being further processed.

The IPG housing 400 may likewise be used as an electrode pole, for example as a reference electrode, and for this purpose is connected via a line 424 to the filter 420.

These signals are added on a weighted basis in the mixer 430, and this result is added to the threshold value detector 440. When the threshold conditions are met, the threshold value detector 440 generates a corresponding detector output signal. This detector output signal is further processed in the evaluation unit 450, and a control signal is sent to the IPG electronics system 410. The IPG electronics system 410 determines the particular function conductors which are to be connected to the filter as input lines. This may once again be externally programmed (see arrow 411).

In the exemplary embodiments illustrated in FIGS. 5A and 5B, the threshold value detector 440 and the evaluation unit 450 together form an evaluation device 460 which responds to an exceedance of the threshold value.

The evaluation device 460 may also be designed in such a way that it determines and evaluates the cumulative effect of the signal by integration, averaging, or determining the effective value of the signal, and outputs an output signal as a function of the magnitude of the cumulative effect.

The threshold value detector 440 may be designed in such a way that it responds to the maximum value of its input signal (the output signal of the mixer 430), and in this sense functions as a maximum value detector.

The IPG electronics system 410, as part of the control device of the cardiac stimulator 10, may be designed in such a way that it always switches the cardiac stimulator 10 to a safe operating mode in the event of an intense electromagnetic field effect, as a function of the output signal of the evaluation unit 450 or of the evaluation device 460, and does so, for example, for a specified, preprogrammed period of time.

The evaluation device 460 may also be connected to a telemetry unit 470 to allow the output signal of the evaluation device to be transmitted to an external device, and thus to provide information for a medical practitioner via a corresponding central service center.

A converter 480 may be mounted at the distal end of the electrode line 405 in the immediate proximity of the particular sensing electrode pole, and the converter converts the signals (differences in potential, for example) detected by the sensing electrode poles in such a way that the signals may be transmitted to the evaluation unit without interference. Such a converter 480 is shown as an optional component in FIGS. 5A and 5B, and is connected to the evaluation unit 450 via a signal line SL.

The converter 480 may be a transformer, for example, which transforms the signal detected by the sensing electrode poles to a higher value in order to conduct the signal to the evaluation unit 450 via high-impedance lines (signal line SL) with immunity to interference from high-frequency alternating fields.

Alternatively, the converter 480 may be a piezoelectric converter which converts the signals detected by the sensing electrode poles into mechanical, specifically acoustic, output signals, for example, which may be conducted to the evaluation unit 450 via a suitable signal line. The evaluation unit 450 may also have an acoustoelectric converter which converts acoustic signals back to electrical signals.

According to another alternative, the converter 480 may be a rectifier or demodulator whose output signal is a direct current signal, so that any high-frequency interferences of this direct current signal may be easily filtered out by the evaluation unit 450.

According to another alternative, the converter 480 may be an electrooptical converter, for example a light-emitting diode (LED), which converts the signal detected by the sensing electrode poles to a light signal, which may be conducted without interference as a signal line SL to the evaluation unit 450 via an optical fiber. In this case the evaluation unit 450 has a complementary converter, for example a photodiode, which converts the light signals back to electrical signals.

The converter for converting the acoustic signal or the light signal to an electrical signal may also be provided at the proximal end of the electrode line 405. This is indicated in FIG. 5B by the converter 490, which is connected to the evaluation unit 450 via an electrical signal line SL'.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implantable medical device having
    a function conductor comprising at least one elongated electrical function conductor configured to transmit therapeutic signals or diagnostic signals or both;
    at least two electrode poles connected to the function conductor, and comprising a field-generating electrode pole configured to deliver electrical current to surrounding bodily tissue and a potential-sensing electrode pole configured to sense electrical potentials in the surrounding tissue;
        wherein said two electrode poles are configured to generate one or more signals;
    a mixer connected to said at least two electrode poles;
    a sensing device which is connected to the field-generating electrode pole and to the potential-sensing electrode pole, and which in an event of a current output via the field-generating electrode pole is configured to detect generated electrical potentials via the potential-sensing electrode pole in relation to a reference potential, and to generate an output signal which represents a detected electrical potential;
        wherein the sensing device includes an evaluation device having a threshold value detector and an evaluation unit,
        wherein said threshold value detector is connected downstream from said mixer,
        wherein said one or more signals are added on a weighted basis in said mixer and a result of said one or more signals added on a weighted basis is generated,
        wherein said result is added to said threshold value detector,
        wherein the evaluation device is configured to evaluate said result to detect specified frequencies above a predetermined threshold to generate said output signal; and,
    a control device connected to the sensing device, wherein said control device is configured to evaluate the output signal generated by the sensing device, and to control the implantable medical device as a function of the detected electrical potentials detected by the sensing device.

2. The implantable medical device according to claim 1, wherein the potential-sensing electrode pole comprises at least one potential-sensing electrode pole, and wherein the field generating electrode pole is one of the at least one potential-sensing electrode pole.

3. The implantable medical device according to claim 1, wherein the potential-sensing electrode pole and the field generating electrode pole are separate electrode poles.

4. The implantable medical device according to claim 1, further comprising a terminal wherein the terminal supplies the reference potential during operation and is associated with the field-generating electrode pole.

5. The implantable medical device according to claim 1, further comprising a terminal wherein the terminal supplies the reference potential during operation and is associated with the potential-sensing electrode pole.

6. The implantable medical device according to claim 1, further comprising a housing, wherein the sensing device is connected to the housing so that during operation the housing supplies the reference potential.

7. The implantable medical device according to claim 1, wherein the potential-sensing electrode comprises at least one potential-sensing electrode and wherein the implantable medical device further comprises a converter that is situated in the immediate proximity of at least one potential-sensing electrode pole wherein the converter converts the generated electrical potentials detected by the at least one potential-sensing electrode pole to a signal which is immune to interference.

8. The implantable medical device according to claim 7, further comprising high impedance lines and wherein the converter is a transformer that is configured to transform the detected generated electrical potentials to a signal comprising higher values in order to conduct the signal comprising higher values via the high-impedance lines to the sensing device.

9. The implantable medical device according to claim 7, wherein the converter is an electroacoustic or a piezoelectric converter that is configured to convert the detected generated electrical potentials to mechanical signals or acoustic signals.

10. The implantable medical device according to claim 9 wherein said implantable medical device is an electrode line having a distal end and a proximal end, wherein the potential-sensing electrode pole is situated in a region of the distal end, and further comprising a second converter that is situated at the proximal end of the electrode line and which is configured to convert the mechanical signals to an electrical signal.

11. The implantable medical device according to claim 7, wherein the converter is a rectifier/demodulator that is configured to convert the detected generated electrical potentials to direct current signals.

12. The implantable medical device according to claim 7, wherein the converter is an electrooptical converter or a light-emitting diode that is configured to convert the detected generated electrical potentials to optical signals or light signals.

13. The implantable medical device according to claim 12 wherein said implantable medical device is an electrode line having a distal end and a proximal end, wherein the potential-sensing electrode pole is situated in a region of the distal end, and further comprising a second converter that is situated at the proximal end of the electrode line and which is configured to convert the optical signals to an electrical signal.

14. The implantable medical device according to claim 1, wherein the evaluation device is configured to determine a cumulative effect of the output signal that represents the detected electrical potential by integration, averaging, or determining an effective value.

15. The implantable medical device according to claim 1, wherein the evaluation device is configured to determine a maximum effect of the output signal that represents the detected electrical potential via said threshold value detector as a maximum value detector.

* * * * *